United States Patent [19]

Fujiwara et al.

[11] Patent Number: 5,399,496

[45] Date of Patent: Mar. 21, 1995

[54] **DNA SHUTTLE VECTORS FOR *E. COLI*, GLUCONOBACTER, AND ACETOBACTER**

[75] Inventors: Akio Fujiwara, Kawasaki; Tatsuo Hoshino, Kamakura; Masako Shinjoh, Yokohama, all of Japan

[73] Assignee: Hoffman-LaRoche Inc., Nutley, N.J.

[21] Appl. No.: 935,144

[22] Filed: Aug. 24, 1992

Related U.S. Application Data

[63] Continuation-in-part of Ser. No. 462,264, Jan. 9, 1990, abandoned.

[30] Foreign Application Priority Data

Feb. 2, 1989 [EP] European Pat. Off. ........... 89101771

[51] Int. Cl.⁶ .................. C12N 15/70; C12N 15/68
[52] U.S. Cl. .................. 435/320.1; 435/172.1; 435/172.2; 435/172.3; 435/252.3; 435/252.33
[58] Field of Search ............ 435/172.2, 172.3, 252.3, 435/252.33, 320.1, 823, 849; 935/22, 23, 52, 66, 72, 73

[56] References Cited

U.S. PATENT DOCUMENTS

4,680,264 7/1987 Puhler et al. ............... 435/172.3

FOREIGN PATENT DOCUMENTS 0276832 1/1988 European Pat. Off. .
0292303 5/1988 European Pat. Off. .
WO89/06688 7/1989 WIPO .

OTHER PUBLICATIONS

Fukaya et al. Agric. Biol. Chem 49(8) 2407–2411 (1985).
Kondorosi et al. Mol. Gen Genet. 188:433–439 (1989).
Kondorosi et al, Mol. Gen. Genet. 188:433–439 (1982) "Mobilization of a *Rhizobium meliloti* Megaplasmid".
J. Ferment. Technol. 63 No. 1, 1–4 (1985).
Fundamental and Applied Biohydrometallurgy, Proceedings of the Sixth International Symposium on Biohydrometallurgy, Vancouver, Aug. 21–24, 1985.
Agric. Biol. Chem., 49(7), 2083–2090 (1985).
European Search Report corresponding to captioned application.

*Primary Examiner*—Margaret Parr
*Assistant Examiner*—Eggerton Campbell
*Attorney, Agent, or Firm*—George M. Gould; William H. Epstein; Catherine A. Picut

[57] ABSTRACT

Novel shuttle vectors which are useful as shuttle vectors among microorganisms belonging to *Escherichia coli*, Gluconobacter and Acetobacter comprising one or more marker genes, a replication origin functional in *Escherichia coli*, a replication origin functional in *Gluconobacter oxydans* and a Mob site.

8 Claims, 5 Drawing Sheets

S: SalI
E: EcoRI
B: BamHI
Bg: BglII
H: HINDIII
Sm: SmaI
DHG: MEMBRANE BOUND L-SORBOSONE DHG GENE
LEGEND ABOVE FOR FIG. 4(a), FIG. 4(b) AND FIG. 4(c)

FIG. 5

DNA SHUTTLE VECTORS FOR E. COLI, GLUCONOBACTER, AND ACETOBACTER

This application is a continuation-in-part of U.S. application Ser. No. 07/462,264, filed on Jan. 9, 1990, which is now abandoned.

FIELD OF THE INVENTION

The present invention is concerned with novel recombinant DNA shuttle vectors which are useful as shuttle vectors among microorganisms belonging to *Escherichia coli*, genus Gluconobacter and genus Acetobacter. The present invention also relates to transconjugants of genus Gluconobacter or genus Acetobacter harboring the shuttle vector DNA or its derivatives. Furthermore, the present invention relates to a process for producing transconjugants of genus Gluconobacter or genus Acetobacter harboring the shuttle vector DNA.

BACKGROUND OF THE INVENTION

A few systems of gene transfer into *Gluconobacter oxydans* were reported in previous publications. Murooka et al. (J. Bacteriol. 145, 358-368 [1981]) reported conjugal mating of a strain of *Gluconobacter oxydans* with a strain of *Escherichia coli* harboring RP4::Mu. The frequency of appearance of a transconjugant was $10^{-10}$/recipient. Fukaya et al. (Agric. Biol. Chem. 49, 2407-2411 [1985]) reported transformation of *Gluconobacter oxydans* with a recombinant plasmid which was constructed from an endogenous plasmid of *Gluconobacter oxydans* and a plasmid of *Escherichia coli*. The transformation frequency was very low (about $10^2$ transformants/μg DNA; in other words, about $10^{-9}$ transformants/recipient). Thus, these systems are not satisfactorily efficient for a gene transfer into *Gluconobacter oxydans*.

Usually, it is required to obtain thousands of transconjugants or transformants in one experiment for a practical use, e.g., for construction of a genomic library.

SUMMARY OF THE INVENTION

In accordance with the present invention, novel and highly useful shuttle vectors are obtained by combining marker genes, a replication origin functional in *Escherichia coli*, a replication origin functional in *Gluconobacter oxydans* and a Mob site.

Thus one aspect of the present invention concerns novel recombinant DNA vectors which comprise a replication origin functional in *Escherichia coli*, a replication origin functional in *Gluconobacter oxydans*, one or more marker genes and a Mob site. The DNA vector may further comprise one or more inserts selected from the group consisting of DNA sequences having multi-cloning sites, expression control sequences, cos sites, terminator sequences, ribosome binding sites, DNA sequences encoding signal peptides and/or proteins. Another aspect of the present invention concerns transconjugants of genus Gluconobacter or genus Acetobacter into which the said vectors are introduced. A further aspect of the present invention concerns a process for producing the said transconjugants which comprises contacting a strain of genus Gluconobacter or genus Acetobacter with a strain of *Escherichia coli* transformed with the vector, under conjugal mating conditions.

The shuttle vectors of the present invention can be transferred among any strains belonging to *Escherichia coli*, genus Gluconobacter and genus Acetobacter, and are replicable in any of these strains.

DETAILED DESCRIPTION OF THE INVENTION

Suitable *Escherichia coli* hosts for the shuttle vectors of the present invention are any strains of *Escherichia coli* used in recombinant DNA technology, e.g., *E. coli* K-12, *E. coli* C600, *E. coli* HB101, *E. coli* ED8767 or *E. coli* S17-1. Suitable Gluconobacter hosts for the shuttle vectors of the present invention are any strains belonging to the genus Gluconobacter. According to the newest classification, all the strains belonging to the genus Gluconobacter fall into the species *Gluconobacter oxydans* (Bergy's Manual of Systematic Bacteriology, Vol. I, 275-278 [1984]; F. Gosselé et al., International J. System. Bacteriol. 33, 65-81 [1983]). Suitable Acetobacter hosts for the shuttle vectors of the present invention are any strains belonging to genus Acetobacter. Preferred strains of the genus Acetobacter are *Acetobacter aceti*, *Acetobacter liquefaciens* and *Acetobacter pasteurianus*.

The vectors of the present invention containing an insert DNA can be maintained stably in the above microorganisms, especially in Gluconobacter strains, even without a selective pressure with antibiotics and the like for a simple and economical industrial process.

It is also very useful that the vectors of the present invention having an origin of replication functional in *Escherichia coli* and an origin of replication functional in *Gluconobacter oxydans* are functional both in *Escherichia coli* and Gluconobacter and Acetobacter strains. *Escherichia coli* is known to be an efficient host for amplification of a vector DNA and manipulation of recombinant DNA by simple and rapid methods. On the other hand, Gluconobacter can be used as a host for expression of Gluconobacter genes. Since the vectors of the present invention are such functional constructs, they enable cloning of certain genes of Gluconobacter or Acetobacter in *Escherichia coli* and thereafter the effective expression of the genes in Gluconobacter or Acetobacter. Furthermore, it is favorable that such functional constructs also contain a DNA region necessary for conjugal transfer (Mob site). Hence the vectors of the present invention can be firstly assembled in *Escherichia coli* and then directly introduced into Gluconobacter or Acetobacter by cunjugal mating without isolation of plasmid DNA from *Escherichia coli*.

Suitable marker genes for the shuttle vectors of the present invention, are all antibiotic resistance genes which are expressed in *Escherichia coli*, Gluconobacter or Acetobacter, such as kanamycin resistance ($Km^r$), streptomycin resistance (Sm$^r$), ampicillin resistance (Ap$^r$) and tetracycline resistance (Tc$^r$).

These antibiotic resistance genes may be isolated from natural or artificially-constructed plasmids, transposons, chromosomal DNAs and synthetic DNAs. Specific sources for the antibiotic resistance genes include but are not limited to plasmids RP4 (Datta et al., J. Bacteriol. 108, 1244–1249 [1971]; NRRL B-18147), RK2 (ATCC 37125), RSF1010 (Nagahari and Sakaguchi, J. Bacteriol. 133, 1527–1529 [1978]; NRRL B-18146), pBR322 (ATCC 31344), pACYC184 (ATCC 37033), pSC101(ATCC 37032), pACYC177 (ATCC 37031), transposons Tn3 (Berg et al., Proc. Nat. Acad. Sci. 72, 3628–3632 [1975]), Tn10 (Foster et al., J. Bacteriol. 124, 1153-1158 [1975]) and their derivatives. As marker genes, pigment-producing genes (e.g. the mel gene on pIJ702 ATCC 35287) may also serve.

Suitable replication origins functional in Escherichia coli for the shuttle vectors of the present invention are, e.g., DNA fragments containing a replication origin of Escherichia coli, or of any plasmid or phage which can autonomously replicate in Escherichia coli. Such replication origins may be isolated, e.g. from plasmids RP4, RSF1010, pBR322, pACYC177, pACYC184, pSC101, λphages (e.g. phage λ, ATCC 10798), P1 phages (e.g. P1 ATCC 25404-B1) or T-coliphages (e.g. coliphage T4 ATCC 11303-B4).

Suitable replication origins functional in Gluconobacter and Acetobacter for the shuttle vectors of the present invention, are e.g., DNA fragments containing a replication origin of Gluconobacter oxydans, or of any endogenous plasmid or phage which can autonomously replicate in Gluconobacter oxydans. Such replication origins may be isolated, e.g. from Gluconobacter oxydans IFO 3293 (FERM P-8356), the endogenous plasmids of Gluconobacter oxydans IFO 3293, or from endogenous Gluconobacter oxydans phage DNAs (Schocher et al., Arch. Microbiol. 121, 193–197 [1979]).

The Mob site is believed to include the origin of transfer (ori T) and to act as a recognition site for certain transactive plasmid's transfer functions (R. Simon et al., Bio/Technology 1, 784–791 [1983]). The Mob site can be obtained from a conjugative plasmid, e.g., plasmids RK2, RP4, RSF1010 or their derivatives. The Mob site-containing plasmid can be transferred from its original host to another host with the help of Tra genes function by using bi-parental conjugal mating or tri-parental conjugal mating. The Tra genes are well known as transfer genes of the broad-host-range IncP-type plasmids, such as plasmids RP4 and RK2. In the bi-parental conjugal mating, Tra genes-containing strains, e.g., E. coli S17-1 (R. Simon et al., supra) harboring Mob site-containing plasmids are mixed with a recipient strain. In the tri-parental conjugal mating, a donor strain harboring Mob site-containing plasmids is mixed with a strain harboring plasmids containing Tra genes, such as RP4 and RK2, and with a recipient strain.

The shuttle vectors of the present invention may also comprise one or more inserts, for example, DNA sequences having multicloning sites, expression control sequences, cos sites, terminator sequences, ribosome binding sites, DNA sequences encoding signal peptides and/or proteins, to add further desirable functions to the shuttle vector.

In more detail, the shuttle vectors of the present invention may comprise DNA sequences including one or more multicloning sites (Messing et al., Methods in Enzymology, 101, 20 [1983]) derived from a variety of plasmids and phages, such as pUC18 (Boehringer Mannheim) or M13mp8 (Boehringer Mannheim), or from synthetic DNA sequences for convenient cloning. Furthermore, the shuttle vectors may contain a wide variety of expression control sequences, such as the lac, trp, tac, or β-lactamase expression control system, control sequences of phage origin, which are, e.g., known from the textbook of Maniatis et al. (Molecular cloning, A Laboratory Manual, Cold Spring Harbor Press, Cold Spring Harbor, N.Y., USA [1982]) or expression control sequences derived from Gluconobacter strains. In addition, the shuttle vectors may contain cos sites for in vitro packaging. Furthermore, they may contain terminator sequences for effective termination, natural or synthetic ribosome binding sites for effective translation, DNA sequences encoding signal peptides for efficient localization of the cloned protein(s) and structural genes of marker proteins all of which are used to construct the efficient Gluconobacter and Acetobacter host-vector systems of the-present invention.

Briefly, the shuttle vectors of the present invention can be obtained by the following steps using the materials as described in the present description and by using recombinant DNA techniques as described by Maniatis et al. (supra):

(1) Preparing a DNA sequence containing marker gene.
(2) Preparing a DNA sequence containing a replication origin functional in Escherichia coli.
(3) Preparing a DNA sequence containing a replication origin functional in Gluconobacter.
(4) Preparing a DNA sequence containing a Mob site.
(5) Combining the DNAs described in (1) to (4) by digesting the said DNA sequences with an appropriate restriction enzyme and ligating them to obtain the recombinant shuttle vectors of the present invention.

By these steps, the shuttle vectors containing marker genes, a replication origin functional in Escherichia coli, a replication origin from Gluconobacter and a functional Mob site can be constructed.

The shuttle vectors of the present invention can be transferred from Escherichia coli to Gluconobacter or Acetobacter with a very high frequency (about $10^{-2}$ to $10^{-1}$ transconjugants per recipient) by a conjugal mating without the isolation and purification of the vector DNA. With these vectors, a genomic library constructed in Escherichia coli ($10^3$-$10^5$ clones) can be transferred into Gluconobacter or Acetobacter in one experiment. Thus, the shuttle vectors of the present invention are highly efficient in viewpoint of simplicity in a cloning experiment.

The most advantageous characteristic of the shuttle vectors of the present invention is their stability in Escherichia coli, Gluconobacter and Acetobacter strains even in the absence of selective pressure. Furthermore, the said vectors affect neither the growth of host cells nor the formation of fermentation products.

In summary, the shuttle vectors of the present invention can be used in industrial processes as vectors for gene cloning and for the production of desired pro- and eukaryotic polypeptides. The desired pro- and eukaryotic polypeptides can be obtained by introducing by transconjugation into a strain of genus Gluconobacter or genus Acetobacter a shuttle vector of the present invention containing the DNA sequence coding for said polypeptide operatively linked with an expression control sequence, culturing the transconjugant under appropriate conditions of growth and isolating the desired polypeptide from the culture

EXAMPLE 1

Construction of the shuttle vector pGE1

*Gluconobacter oxydans* (*G. oxydans*) IFO 3293 contains two kinds of cryptic plasmids which are maintained stably in the cell without any selective pressure. The smaller plasmid designated pGO3293S is a relaxed type plasmid (the copy number is more than 10) and its molecular size is 9.9kb. The larger plasmid designated pGO3293L is a stringent type plasmid (the copy number is 1 to 2) and its molecular size is about 60kb. Considering the appropriate copy number and DNA size of the said vectors pGO3293S was selected as source for the replication origin functional in *G. oxydans*.

Plasmid pSUP301 was used as source for the replication origin functional in *Escherichia coli* (*E. coli*), the antibiotic resistance genes ($Km^r$ gene and $Ap^r$ gene) and the Mob site. Plasmid pSUP301 was constructed by combining pACYC177 with a Mob site derived from RK2 (R. Simon et al., supra). Therefore, plasmids pACYC177 and RK2, or the like, can be used in place of plasmid pSUP301.

A) Preparation of plasmids pGO3293S and pSUP301

Plasmid pSUP301 was prepared from *E. coli* cells harboring plasmid pSUP301 by the alkaline method (H. C. Birnboim and J. Doly, Nucleic Acids Research, 7, 1513–1523 [1979]).

Plasmid pGO3293S was prepared from *G. oxydans* IFO 3293 cells by the alkaline method as described below:

*G. oxydans* cells were cultivated in a test tube containing 5 ml of mannitol broth (MB) medium containing 25 g/l mannitol, 5 g/l yeast extract (Difco), and 3 g/l Bactopeptone (Difco) for 24 hours at 30° C.. Then, 4 ml of the culture broth were transferred into a 500 ml Erlenmeyer flask containing 50 ml of fresh MB medium. The flask was incubated at 30° C. for 15 hours on a rotary shaker operating at 180 rpm The resulting broth was centrifuged at 5,000 rpm (3,000 g) for 15 minutes. The cells were suspended in 10 ml of solution I (25 mM Tris-HCl, pH 7.9, containing 2 mg/ml lysozyme, 5 mM glucose, 10 mM EDTA). The cell suspension was kept on ice for 30 minutes. Then, 20 ml of solution II (18 mM NaOH containing 1% SDS) were added. The solution was kept on ice for 10 minutes and added with 15 ml 3M sodium acetate, pH 4.8. The resulting solution was kept on ice for 60 minutes and was centrifuged at 13,000 rpm (21,000 g) for 10 minutes. 40 ml of isopropanol were added to the supernatant (40 ml). The mixture was kept on ice for 60 minutes and centrifuged at 15,000 rpm (28,000 g) for 15 minutes. The pellet was dried and dissolved in 2 ml of distilled water. The plasmid DNA was further purified by ethanol precipitation to obtain a final plasmid DNA solution.

B) Construction of a composite plasmid using plasmids pGO3293S and pSUP301

150 ng of pSUP301 DNA and 200 ng of pGO3293S DNA were completely digested with HincII and ligated with T4 DNA ligase. The resulting ligation mixture was used to transform *E. coli* S17-1.

$Km^r$ transformants were first selected on LK (Luria broth containing 50μg/ml kanamycin; Luria broth (LB): 10 g/l bactotryptone, 5 g/l yeast extract, 5 g/l NaCl) agar plates Then, $Ap^sKm^r$ clones, i.e. transformants carrying a plasmid with an insert in the $Ap^r$ gene, were selected using both LK agar plates and LA (LB medium containing 50 μg/ml ampicillin) agar plates.

c) Transfer of composite plasmids from *E. coli* to *G. oxydans* by bi-parental conjugation A mixture of composite plasmids obtained from all the $Km^r$, $Ap^s$ transformants were transferred to *G. oxydans* N44-1 (a 2-KGA high producer mutant strain obtained from *G. oxydans* IFO 3293 by mutagenesis as described in European Patent Application, Publication No. 213 591 the teaching of which are incorporated herein by reference) by a bi-parental conjugal mating. Bi-parental conjugal mating was carried out as follows:

Two hundred μ of a log phase culture of the recipient *G. oxydans* N44-1 grown in MB medium were mixed with 100 μl of log phase culture of all the $Km^r$ transformants grown in LB medium containing 5 μg/ml kanamycin and 10 μg/ml streptomycin and spotted onto nitrocellulose filter on the surface of FB (50 g/l fructose, 10 g/l yeast extract, 10 g/l polypeptone) agar plates. The plates were incubated overnight at 30° C. The mixed colonies were plated onto MB containing 10 μg/ml polymyxin B and 50 μg/ml kanamycin (MPK) agar plates, and MB containing 10 μg/ml polymyxin B (MP) agar plates after an appropriate dilution, and incubated for 4 days at 30° C.

The frequency of the conjugation was calculated as a ratio of number of colonies on MPK agar plates to number of colonies on MP agar plates.

The frequency of this experiment was 0.06–0.1% (transconjugant per recipient). The plasmid DNAs were prepared from 5 transconjugants by mini-alkaline method and analyzed by agarose gel electrophoresis. Consequently, all the plasmids tested had the same structure. One plasmid was designated pGE1. Plasmid pGE1, as described above and illustrated in FIG. 1, is deposited in The National Institute of Bioscience and Human Technology, Agency of Industrial Science and Technology, 1-3 Higashi 1 Chome Yatabe-Machi Tsukuba-gun, Ibaraki-ken 305, Japan as Ferm BP-4765 on Aug. 6, 1994, under the Budapest Treaty.

D) Characterization of the newly-isolated plasmid pGE1

Figure 1:
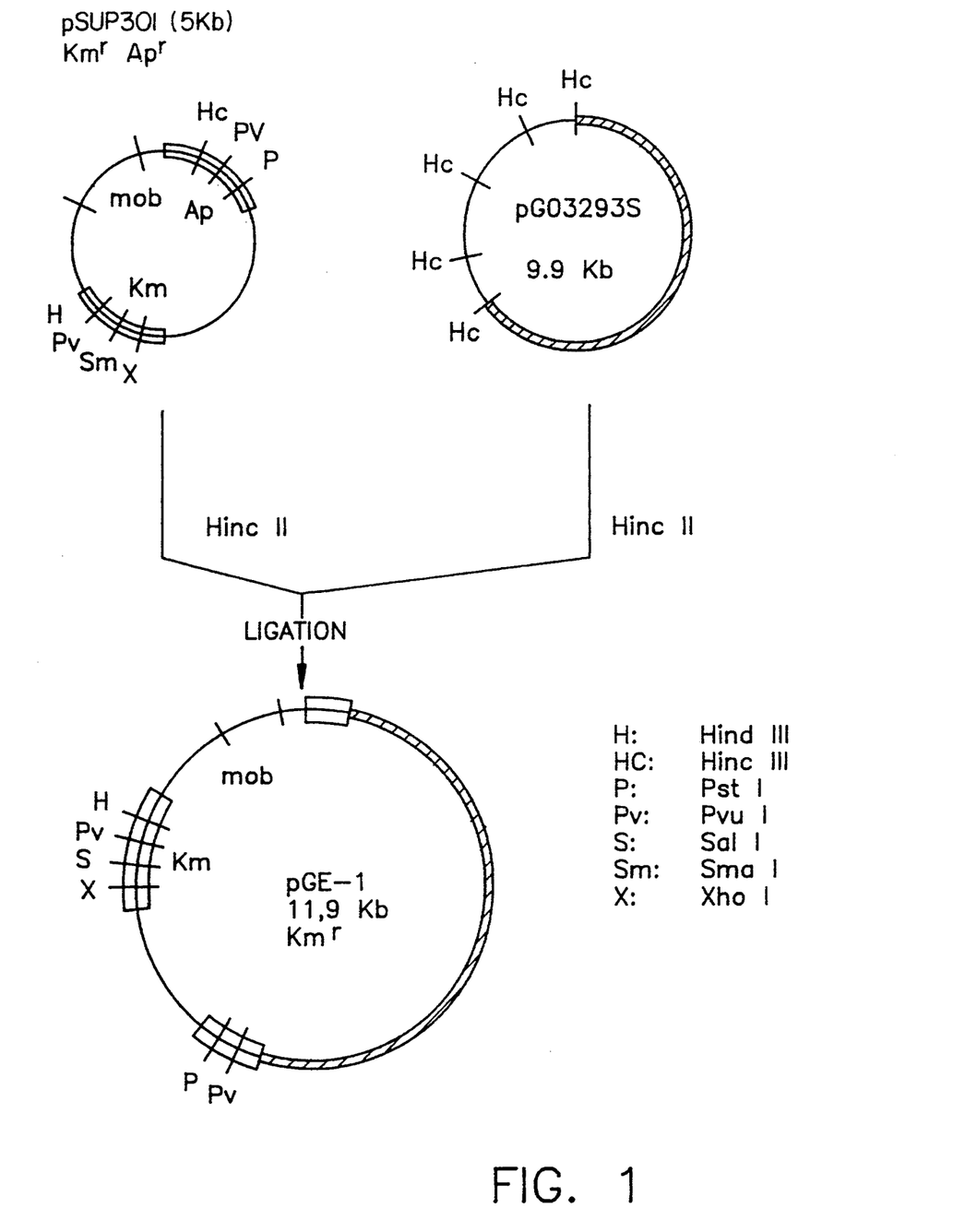
FIG. 1 illustrates the construction of the shuttle vector, pGE1.

Plasmid pGE1, prepared from cells of *G. oxydans* N44-1 harboring pGE1, was introduced into *E. coli* strain C600 by transformation to confirm if it is a shuttle vector between *G. oxydans* and *E. coli* or not. *E. coli* strain C600 was transformed with plasmid pGE1 at a frequency of $10^6$ transformants per μg DNA. This finding indicated that pGE1 worked as a shuttle vector between *E. coli* and *G. oxydans*. The schematic presentation of construction of pGE1 is shown in FIG. 1.

DNA sequences of pGE1 prepared from cells of *G. oxydans* N44-1 and *E. coli* S17-1 harboring pGE1 were digested with AvaI, HincII, PstI, PvuI or PvuII and were analyzed by agarose gel electrophoresis. The DNA fragments were Southern-transferred to nitrocellulose filters. The HincII fragments, PstI fragments and non digested DNA were hybridized with $^{32}$P-labeled pSUP301, while the PvuI, PvuII and AvaI fragments were hybridized with $^{32}$P-labeled pGO3293S.

The autoradiogram clearly showed that pGE1 contains the DNA fragments derived from both pSUP301 nd pGO3293S and that pGE1 exists in the same structure in both *E. coli* and *G. oxydans*. Neither modifications nor deletions were noted.

EXAMPLE 2

Conjugal transfer of plasmid pGE1 and other plasmids into G. oxydans

Efficiencies of conjugal transfer of various vectors were compared to characterize plasmid pGE1.

Five plasmids, viz. RP4, RSF1010, pVK102 (ATCC 37158), pSUP301 and pGE1, were transferred from *E. coli* to *G. oxydans* N44-1 using the conjugal transfer system. The best frequency of the conjugal transfer of each plasmid is shown in Table 1. Plasmid pSUP301 could not be introduced into Gluconobacter because a replication origin for Gluconobacter is absent in this plasmid. On the other hand, plasmid pGE1 as well as plasmids RP4, RSF1010, pVK102 were transferred into Gluconobacter at the high frequency of $10^{-2}$ to $10^{-1}$ (transconjugants per recipient).

TALBE 1

| Vector | Frequency of the conjugal transfer | |
|---|---|---|
| | Mwt (kb) | Frequency (Transconjugants/recipient) |
| RP4 | 56 | $10^{-2} - 10^{-1}$ |
| RSF1010 | 8.9 | $10^{-1}$ |
| pVK102 | 23 | $10^{-2} - 10^{-1}$ |
| pSUP301 | 5 | $<10^{-6}$ |
| pGE1 | 11.0 | $10^{-1}$ |

EXAMPLE 3

Effect of plasmid pGE1 on cell growth and 2-KGA production

New plasmid pGE1 and plasmids RP4, RSF1010 and pVK102 were introduced into *G. oxydans* N44-1 as described in the Example 1-(C). The transconjugants were transferred from MB agar plates containing antibiotics into test tubes containing 5 ml of No. 5 medium (80 g/l L-sorbose, 0.5 g/l glycerol, 15 g/l yeast extract, 2.5 g/l MgSO$_4$.7H$_2$O, 15 g/l CaCO$_3$) with or without antibiotics. The test tubes were incubated on a shaker at 30° C. for 5 days. N44-1 was also cultivated in the No. 5 medium in the same way as a control but without antibiotics. The fermentation broth was assayed for cell growth and 2-KGA production by determining the optical density at 550 nm (OD$_{550}$), and the 2-KGA amount.

As shown in Table 2, plasmid pGE1 is the best vector for the maintenance of growth and 2-KGA production among the vectors tested. In contrast, the presence of RP4 caused the reduction of both cell growth (by 20%) and 2-KGA production (by 45%). In addition, another defect was found in RP4; deletion of RP4 occurred when it replicated in Gluconobacter.

RSF1010 and pVK102 did not affect the growth but often lowered the 2-KGA productivity of N44-1 to 80% and 90% of the level of the standard, respectively.

TABLE 2

Effect of the presence of various vectors on growth and 2-KGA production

| Host | Vector | OD550 | | 2-KGA (g/l) | |
|---|---|---|---|---|---|
| | | Antibiotic* | | | |
| | | + | − | + | − |
| N44-1 | — | — | 21.1 | — | 52.1 |
| | RP4 | 14.1 | 15.9 | 26.0 | 31.8 |
| | RSF1010 | 20.4 | 20.8 | 42.7 | 43.3 |
| | pVK102 | 20.1 | 20.5 | 48.8 | 48.1 |
| | pGE1 | 20.2 | 20.8 | 54.4 | 55.9 |

*Antibiotic for RP4, pVK102 and pGE1 was kanamycin (50 μg/ml) and that for RSF1010 was streptomycin (50 μg/ml).

Stability of plasmid pGE1 during cultivation N44-1-transconjugants described in Example 3 were cultivated in Km-free broth, diluted and plated on MB agar plates. The plates were incubated at 30° C. for 5 days. *E. coli* strain S17-1 harboring plasmid pGE1 was cultivated in Km-free LB medium, diluted and plated on LB agar plates. The plates were incubated at 37° C. for 1 day.

The resulting colonies were used to determine the stability of the plasmids as follows:

Plasmid stability was defined as the ratio of the number of colonies grown on agar plates containing antibiotics to that of colonies grown on agar plates without antibiotics.

Liquid samples withdrawn from the culture broth at various stages of cultivation were appropriately diluted, plated on antibiotics-free agar plates and incubated at 37° C. for one day (*E. coli*) or at 28° C. for five days (*G. oxydans*). One hundred colonies grown on these plates were transferred onto agar plates with and without antibiotics. The plates were incubated in the same conditions as described above and the number of colonies which appeared was counted for the calculation of plasmid stability.

Table 3-(a) shows that RP4 was extremely unstable in the 2-KGA high producer N44-1 but stable in the 2-KGA non-producer C20 (a mutant strain obtained from *G. oxydans* IFO 3293 by mutagenesis as described in European Patent Application, Publication No. 213 591 the teachings of which are incorporated herein by reference). The other vectors were considerably stable in both strains.

However, in our previous experiments, it was noted that RSF1010 with an insert was often cured or deleted (data not shown). Therefore, pGE1 and pVK102 were further studied concerning the stabilities during cultivation.

N44-1 cells harboring plasmids pVK102, p7A6Δ4 (derivative of pVK102 containing the gene for membrane-bound sorbosone dehydrogenase; for construction see Example 8) or pGE1 were cultivated in MB liquid medium with 50 μg/ml kanamycin in test tubes for 2 days to prepare a seed culture. One tenth ml of the seed culture was transferred to 5 ml of Km-free MB medium in a test tube. The test tube was incubated at 30° C. for 1 day on a tube shaker. Three cycles of this transfer and cultivation were carried out in MB medium. One tenth ml of the same seed culture was also transferred to 5 ml of Km-free No. 5 medium in a test tube to test plasmid stability under 2-KGA producing condition. Three cycles of transfer and cultivation (at 30° C. for 2 to 3 days) were also carried out in No. 5 medium. At the end of each cultivation, the broth was appropriately diluted and plated on MB agar plates to determine the stability of the plasmid used.

Table 3-(b) shows that plasmid pGE1 was extremely stable (100%) under the examined conditions, while pVK102 and p7A6Δ4 were considerably, but to a lesser extent, stable (74–100%). These results indicate that the 2-KGA fermentation can be carried out by the 2-KGA high producer harboring pGE1 without the addition of kanamycin in the practical process which includes 2 to 3 cycles of seed cultivations. Plasmid pGE1 was also very stable (100%) in E. coli during three cycles of cultivations without antibiotics.

TABLE 3-(a)

Stability of various vectors during cultivation
Stability during cultivation in No. 5 medium (%)

| Host | RP4 a) (Km$^r$) b) (Tc$^r$) | RSF1010 (Sm$^r$) | pVK102 (Km$^r$) | pGE1 (Km$^r$) |
|---|---|---|---|---|
| N44-1 | a) 18% b) 18% | 100% | 78% | 90% |
| C-20 | a) 100% b) 100% | 89% | 84% | NT |

TABLE 3-(b)

Stability during cultivation in MB medium (%) and No. 5 medium (%)

| Plasmid | Transfer No. | Plasmid stability in: MB medium | No. 5 medium |
|---|---|---|---|
| pVK102 | 1 | 98 | 96 |
|  | 2 | 96 | 94 |
|  | 3 | 90 | 74 |
| p7A6Δ4 | 1 | 98 | 92 |
|  | 2 | 100 | 100 |
|  | 3 | 94 | 88 |
| pGE1 | 1 | 100 | 100 |
|  | 2 | 100 | 100 |
|  | 3 | 100 | 100 |

N44-1-harboring each plasmid was cultivated in mannitol broth (MB) for 1 day or in No. 5 medium for 2 to 3 days and 2% of the broth was transferred into each fresh medium.

EXAMPLE 5

Compatibility of plasmid pGE1 with plasmid pVK102

Compatibility of plasmid pGE1 with plasmid pVK102 was examined since the introduction of 2-KGA fermentation-relating genes into one host strain will presumably require two or more vectors which are compatible.

Plasmid pVK102 was transferred by bi-parental conjugal mating from E. coli S17-1 to G. oxydans IFO 3293 which harbored plasmid pGE1. Transconjugants were selected on the basis that the bacteria showed both kanamycin- and tetra-cycline-resistances. Plasmid DNAs prepared from Km$^r$ and Tc$^r$ transconjugants were used to transform E. coli S17-1 to confirm the presence of both plasmids in the transconjugants. Among the transformants, there were pGE1 and pVK102-harboring ones as expected. These findings indicate that plasmid pGE1 is compatible with plasmid pVK102 in Gluconobacter.

EXAMPLE 6

Host range of plasmid pGE1

Plasmid pGE1 was conjugal-transferred from E. coli S17-1 into various strains belonging to genus Gluconobacter, viz. G. oxydans IFO3293, G. oxydans IFO3462, G. oxydans IFO3268, G. oxydans IFO3271, G. oxydans IFO3287, G. oxydans IFO 3172 and G. oxydans ATCC9937 and into various strains belonging to genus Acetobacter, viz. A. liquefaciens IHO 12258 (ATCC23750) A. acetosus IFO3129, A. pasteurianus IFO3170, A. pasteurjanus IFO3223 and A. pasteurjanus IFO3225 by a bi-parental conjugal mating as described in Example 1(C).

Km$^r$ colonies were obtained from all strains of Gluconobacter and Acetobacter. Then, the plasmid DNAs of obtained Km$^r$ strains were analyzed for their characteristics in comparison with the original plasmid pGE1.

The plasmid DNAs were subjected to agarose gel electrophoresis. The analysis showed that all the plasmids had the same molecular size as plasmid pGE1. The DNA bands on agarose gel were transferred to nylon filter and subjected to Southern-hybridization analysis. All the DNA bands hybridized with $^{32}$P-labeled plasmid pGE1DNA. Thus, all the Km$^r$strains obtained from the strains of Gluconobacter and Acetobacter were confirmed to be transconjugants harboring plasmid pGE1.

Plasmid DNAs isolated from each transconjugant were used to transform E. coli strain C600. Km$^r$ transformants obtained were cultivated in LK liquid medium at 37° C. one overnight. Plasmid DNA was extracted from each tranformant and analyzed by agarose gel electrophoresis after digestion with Bgl II. All plasmid DNAs examined were confirmed to be identical with plasmid pGE1DNA. Neither deletion nor insertion of DNA were observed. Consequently, plasmid pGE1 works as a shuttle vector for various Gluconobacter and Acetobacter strains.

EXAMPLE 7

Stability of plasmid pGE1 in various strains belonging to genus Gluconobacter and Acetobacter Every transconjugant described in Example 6 maintained on MB agar plate containing kanamycin (50 μg/ml) was transferred into MB liquid medium containing 50 μg/ml kanamycin in a test tube and cultivated for 2 days to prepare a seed culture. One tenth ml of the seed culture was transferred to 5 ml of kanamycin-free MB medium. The test tube was incubated at 3° C. for 1 day on a tube shaker. Three cycles of this transfer and cultivation were carried out in MB medium. The seed culture, first culture and third culture were appropriately diluted and spread on MB agar plates to determine the stability of the plasmid pGE1 as shown in Example 4.

Table 4 shows that plasmid pGE1 was extremely stable (100%) in G. oxydans IFO3293, G. oxydans IFO3268 and A. acetosus IFO3129 and considerably stable (68-98%) in G. oxydans IFO3462, G. oxydans IFO3271, G. oxydans IFO3287, G. oxydans IFO3172, G. oxydans ATCC9937, A. pasteurianus IFO3170, A. pasteurianus IFO3223 and A. pasteurianus IFO3225 even after three transfers without kanamycin selection.

TABLE 4

Stability of plasmid pGE1 in various strains belonging to genus Gluconobacter and czenus Acetobacter

|  |  | Plasmed-harboring strains (%) | | |
|---|---|---|---|---|
|  |  | in seed cul.$^{a)}$ | 1st cul.$^{b)}$ | 3rd cul.$^{b)}$ |
| G. oxydans | IFO 3293 | 100 | 100 | 100 |
| " | IFO 3462 | 100 | 94 | 88 |
| " | IFO 3268 | 100 | 100 | 100 |
| " | IFO 3271 | 86 | 82 | 68 |
| " | IFO 3287 | 100 | 100 | 94 |
| " | IFO 3172 | 96 | 98 | 96 |
| " | ATCC 9937 | 100 | 96 | 92 |
| A. acetosus | IFO 3129 | 100 | 100 | 100 |

TABLE 4-continued

Stability of plasmid pGE1 in various strains belonging to genus Gluconobacter and czenus Acetobacter

| | | Plasmed-harboring strains (%) | | |
|---|---|---|---|---|
| | | in seed cul.[a] | 1st cul.[b] | 3rd cul.[b] |
| A. pasteurianus | IFO 3170 | 96 | 76 | 86 |
| " | IFO 3223 | 100 | 98 | 96 |
| " | IFO 3225 | 100 | 98 | 100 |

[a] Seed culture was carried out in MB medium containing 50 μg/ml kanamycin.
[b] First and third cultures were carried out in MB medium without kanamycin.

EXAMPLE 8

Use of plasmid pGE1 as a cloning vector

A) Integration of membrane-bound L-sorbosone dehydrogenase gene into plasmid pGE1

The cloned gene of membrane-bound L-sorbosone dehydrogenase of A. liquefaciens IFO 12258 was introduced into plasmid pGE1 to demonstrate its usefulness as a cloning vector.

The BglII fragment (5.5kb) containing membrane-bound L-sorbosone dehydrogenase (SNDH) gene was isolated from plasmid p7A6Δ4 and ligated with plasmid pGE1 partially digested by BglII. The resulting DNA mixture was used to transform E. coli S17-1. Five hundred (500) transformants were picked and transferred onto nitrocellulose filters placed on the surface of LSK (LB medium containing 100 μg/ml streptomycin and 50 μg/ml kanamycin) agar plates and incubated at 37° C. overnight. The filters were treated with 0.5M NaOH-1.5M NaCl solution for 5 minutes and neutralized with 3M sodium acetate (pH 4.8) for 5 minutes. Colony-blotted filters were used for hybridization with $^{32}$P-labeled 1.8kb SalI fragment which was isolated from p7A6Δ4 and contained only DNA of A. liquefaciens IFO 12258. Fifteen positive clones were selected and their plasmids were analyzed by digestion with BglII or PvuI.

Figure 2:
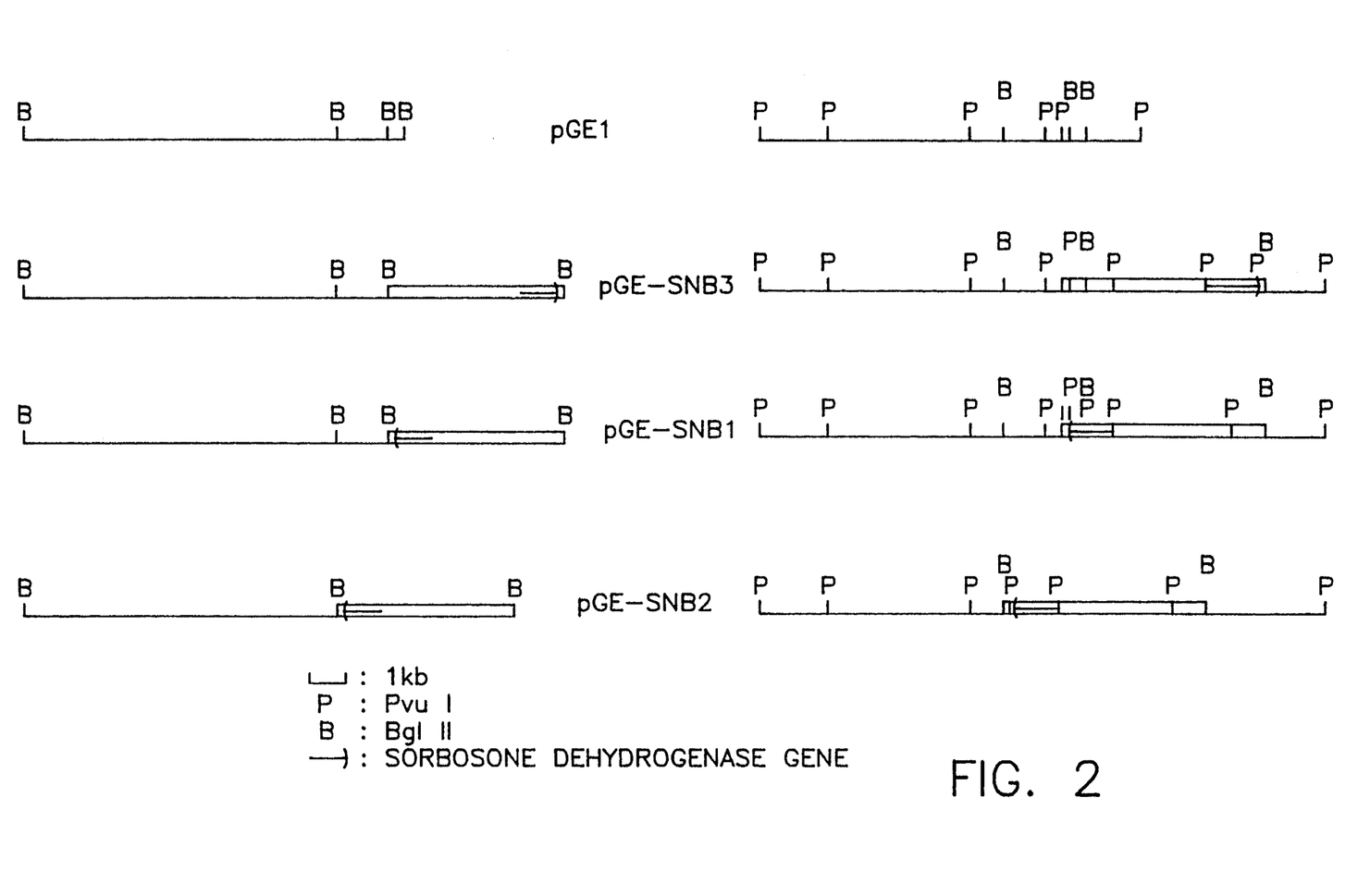
FIG. 2 illustrates the insertion of the membrane-bound L-sorbosone dehydrogenase gene into plasmid pGE1.
Figure 3:
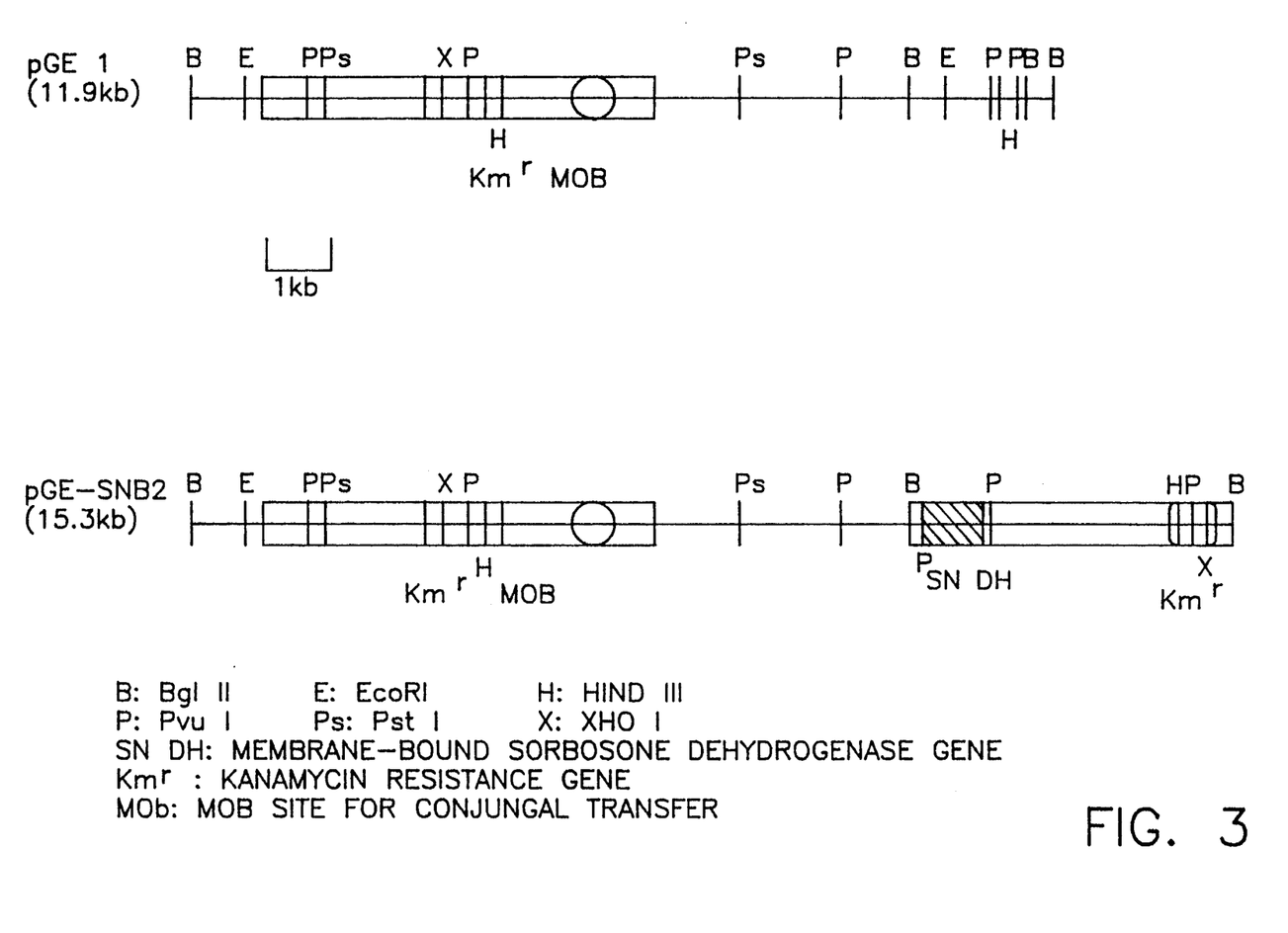
FIG. 3 represents the restriction maps of plasmids pGE1 and pGE-SNB2.
Figure 4A:
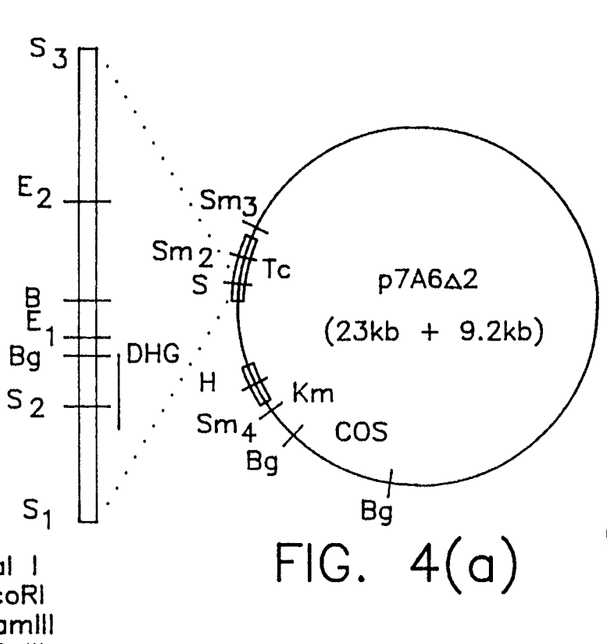
FIG. 4 illustrates the restriction maps of plasmids p7A6Δ2, p7A6Δ3 and p7A6Δ4.
Figure 4B:
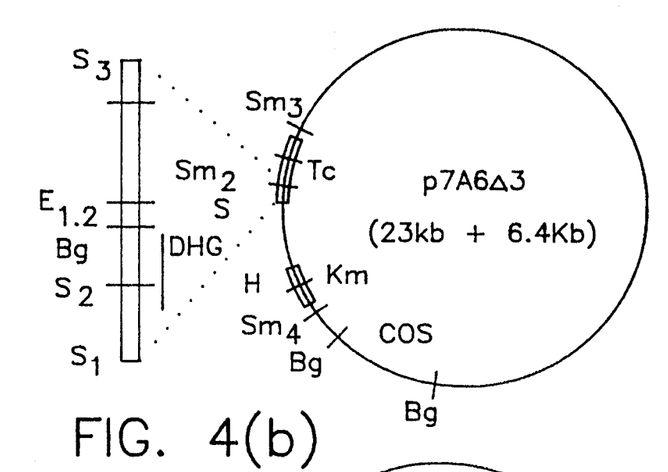
Figure 4C:
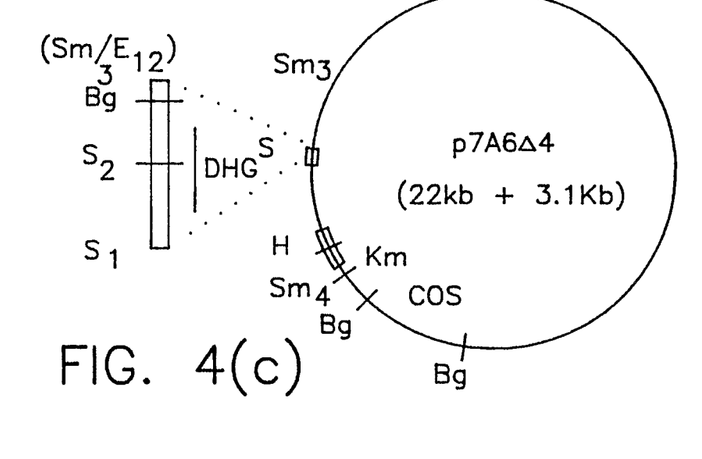

As shown in FIG. 2, three types of subclones were isolated which are hereafter referred to as pGE-SNB1, pGE-SNB2 and pGE-SNB3. All of them contained a 5.5 kb BglII fragment. Simultaneously, they, however, lost 1.7 kb and/or 0.4 kb BglII fragments from plasmid pGE 1, which consists of 3 BglII fragments (9.8 kb, 1.7 kb and 0.4 kb). Therefore, plasmid pGE1 can be shortened to 9.8 kb as a viable vector by BglII digestion. The detailed restriction maps of pGE1 and pGE-SNB2 are shown in FIG. 3.

B) Effect of subclones on 2-KGA production in a resting system

The effect of SNDH gene-containing pGE1 derivatives carried in N44-1 on 2-KGA production was examined in comparison with that of plasmids pGE1, pVK102 or p7A6Δ4 carried in N44-1. Two natural strains possessing an efficient membrane-bound L-sorbosone dehydrogenase, A. liquefaciens (ATCC 23750) and Pseudomonas putida (P. putida) (ATCC 21812; Makover et al., Biotechnol. Bioeng. 17, 1485-1514 [1975]) were also used as control strains.

Three subclones of SNDH gene-containing plasmids pGE-SNB1, pGE-SNB2 and pGE-SNB3, as well as plasmids pGE1, pVK102 and p7A6Δ4 were transferred from E. coli S17-1 into G. oxydans IFO 3293 by bi-parental conjugal mating. The transconjugants, A. liquefaciens (ATCC 23750) and P. putida (ATCC 21812) were cultivated in MB overnight. Cells were then diluted to an OD$_{550}$=2 and cells collected from 4 ml of the cell suspension were resuspended in 4 ml of reaction mixture containing 18 g/l L-sorbosone, 10 g/l CaCO$_3$ and 3 g/l NaCl and incubated at 30° C. Table 5 shows the amounts of 2-KGA produced after 2, 20 and 63 hours.

The 2-KGA productivities of transconjugants containing SNDH gene containing subclones pGE-SNB1, pGE-SNB2 and pGE-SNB3 were better than those of A. liquefaciens (ATCC 23750) and P. putida (ATCC 21812). Furthermore, 2-KGA production by these subclones was almost as good as 2-KGA production of plasmid p7A6Δ.

When the said subclones were introduced into N44-1, a 2-KGA high producer, they showed better 2-KGA yields than N44-1 either from L-sorbose or L-sorbosone under the resting system as shown in Table 6. Molar yield of 2-KGA from L-sorbosone by strain with SNDH gene-containing plasmid was 90%, whereas molar yield by strain with a vector plasmid only was 20%. Molar yield of 2-KGA from L-sorbose by SNDH gene-containing strain was 60 to 70% whereas that of SNDH gene-free strain was about 40%.

TABLE 5

Comparison of 2-KGA production rate from L-sorbosone under a resting system

| | | 2-KGA (g/l) / 2 OD$_{550}$ | | |
|---|---|---|---|---|
| | | 2 hr. | 20 hr. | 63 hr. |
| G. oxydans | IFO 3293 | — | 0.0 | 2.1 | 1.9 |
| | pVK102 | 0.0 | 1.3 | 1.1 |
| | p7A6Δ4 | 1.6 | 15.8 | 19.1 |
| | pGE1 | 0.0 | 1.5 | 3.2 |
| | pGE-SN B1 | 1.8 | 18.4 | 19.4 |
| | pGE-SN B2 | 1.3 | 10.7 | 15.4 |
| | pGE-SN B3 | 1.8 | 17.2 | 19.2 |
| A. liquefaciens | ATCC 23750 | — | 0.9 | 6.4 | 8.9 |
| P. putida | ATCC 21812 | — | 0.9 | 7.4 | 10.0 |

L-Sorbosone: 18 g/l
Temperature: 30° C.

TABLE 6

2-KGA Production from L-Sorbosone or L-Sorbose by N44-1 carrying various plasmids under a resting system

| | 2-KGA produced (g/l) from | |
|---|---|---|
| | 36 g L-Sorbosone | 40 g/l L-Sorbose |
| G. oxydans N44-1 | | |
| — | 13.0 | ND |
| pVK102 | 7.6 | 19.9 |
| p7A6Δ4 | 33.8 | 31.2 |
| pGE1 | 8.5 | ND |
| pGE-SN B1 | 31.8 | 30.3 |
| pGE-SN B2 | 35.5 | 25.4 |

ND: Not determined

Reaction from L-sorbosone or L-sorbose was carried out at 30° C. for 1 day or for 6 days, respectively.

EXAMPLE 9

Construction of plasmid p7A66 4

(A) Construction of a cosmid genomic library in E. coli S17-1

A. liquefaciens ATCC23750 was cultivated in 200ml of mannitol broth (MB) (25 g/l of mannitol, 3 g/l of bactopeptone, 5g/l of yeast extract) for 48 hours at 30° C. The cells were collected by centrifugation, washed with 100ml of Tris (10 mM)-EDTA (1 mM) buffer, pH 7.5 and resuspended in 50ml of Tris (10 mM)-EDTA (20 mM) buffer, pH 7.5.

The cell suspension thus prepared was treated with 2 ml of the lysozyme solution (10 mg/ml) at 37° C. for 30 minutes followed by the treatment with pronase (4000 units) at 37° C. for 30 minutes and 10ml of 5% SDS at 37° C. for 1 hour. At this point, a clear lysate was obtained. DNA was extracted with 60ml of neutral phenol:chloroform containing 4% octanol (1:1) by rotating slowly at 4° C. for 30 minutes. The mixture was centrifuged at 15000rpm (28,000 g) for 15 minutes and the supernatant obtained was extracted with 60ml of chloroform:octanol (96:4) by rotating slowly at 4° C. for 10 minutes.

To the 50ml supernatant obtained by centrifugation at 15000rpm (28,000 g) for 15 minutes were added 5ml of 3M sodium acetate and 55ml of cold ethanol. The crude DNA was obtained by winding out with a glass rod, which was then treated with RNase T1 and A (37° C., 30 minutes) and pronase (37° C., 30 minutes) again. The phenol and chloroform extractions were repeated to obtain pure chromosomal DNA.

The chromosomal DNA of *A. liquefaciens* ATCC23750 was partially digested with Sal I. The resulting fragments of 15kb to 35kb were isolated from agarose gel by electrophoresis. Plasmid pVK102 (ATCC 37158) DNA was completely digested with Sal I and dephosphorylated with calf intestine alkaline phospha- tase. The DNA fragments of 15kb to 35kb and the linear pVK102 DNA were ligated with T4 DNA ligase.

The ligated fragments were used for in vitro packaging using a packaging kit (Amersham International plc) and the resulting phage particles were incubated with *E. coli* ED8767 (Murray et al., Mol. Gen. Genet. 150, 53, 1977). The cell suspension was plated on to LB agar plates containing 50µg/ml kanamycin.

One thousand Km$^r$ colonies were scraped and used to prepare a mixture of recombinant plasmids. The plasmid DNAs were used to transform *E. coli* S17-1 (Sm$^r$ Tra+). One thousand and four hundred transformants were picked into microtiter plates containing LB medium with 100 µg/ml of streptomycin and 50µg/ml of kanamycin, incubated overnight and stored with 15% glycerol at -80° C. as the genomic library of *A. liquefaciens* ATCC23750 in *E. coli* S17-1. The average size of the inserts was 25kb to 30kb.

(B) Conjugal transfer of the cosmid genomic library in *E. coli* S17-1 into *G. Oxydans* OX-4

The cosmid genomic library of *A. liquefaciens* ATCC23750 in *E. coli* S17-1 was transferred to *G. oxydans* OX-4 (a L-sorbosone accumulating mutant obtained from *G. oxydans* IFO 3293 by mutagenesis as described in European Patent Application, Publication No. 213 591 the teachings of which are incorporated herein by reference) using bi-parental mating between both strains.

Two hundred µl of log phase culture of the recipient *G. oxydans* OX-4 grown in mannitol broth were mixed with 100 µl of log phase culture of every *E. coli* S17-1 carrying pVK102 with insert DNA individually and spotted onto nitrocellulose filter on the surface of fructose broth (50 g/l fructose, 5 g/l yeast extract, 5g/l polypeptone) agar plates. The plates were incubated overnight at 30° C. The mixed colonies were streaked onto MB containing 10 µg/ml polymyxin B and 50 µg/ml kanamycin (MPK) agar plates and incubated for 4 days at 30° C. The resulting transconjugants were purified by restreaking on MPK agar plates.

Screening was carried out using a mini-resting system. About 1400 strains of *G. oxydans* OX-4/pVK102 with insert DNA were suspended in the reaction mixture containing 50 µl of 3 g/l of NaCl, 10 g/l of CaC03 and 30 g/l of L-sorbose or L-sorbosone individually and incubated for 1 to 5 days at 30° C. Assays for 2-KGA production were performed by thinlayer chromatography on silica gel. One positive clone, p7A6, was obtained.

Figure 5:
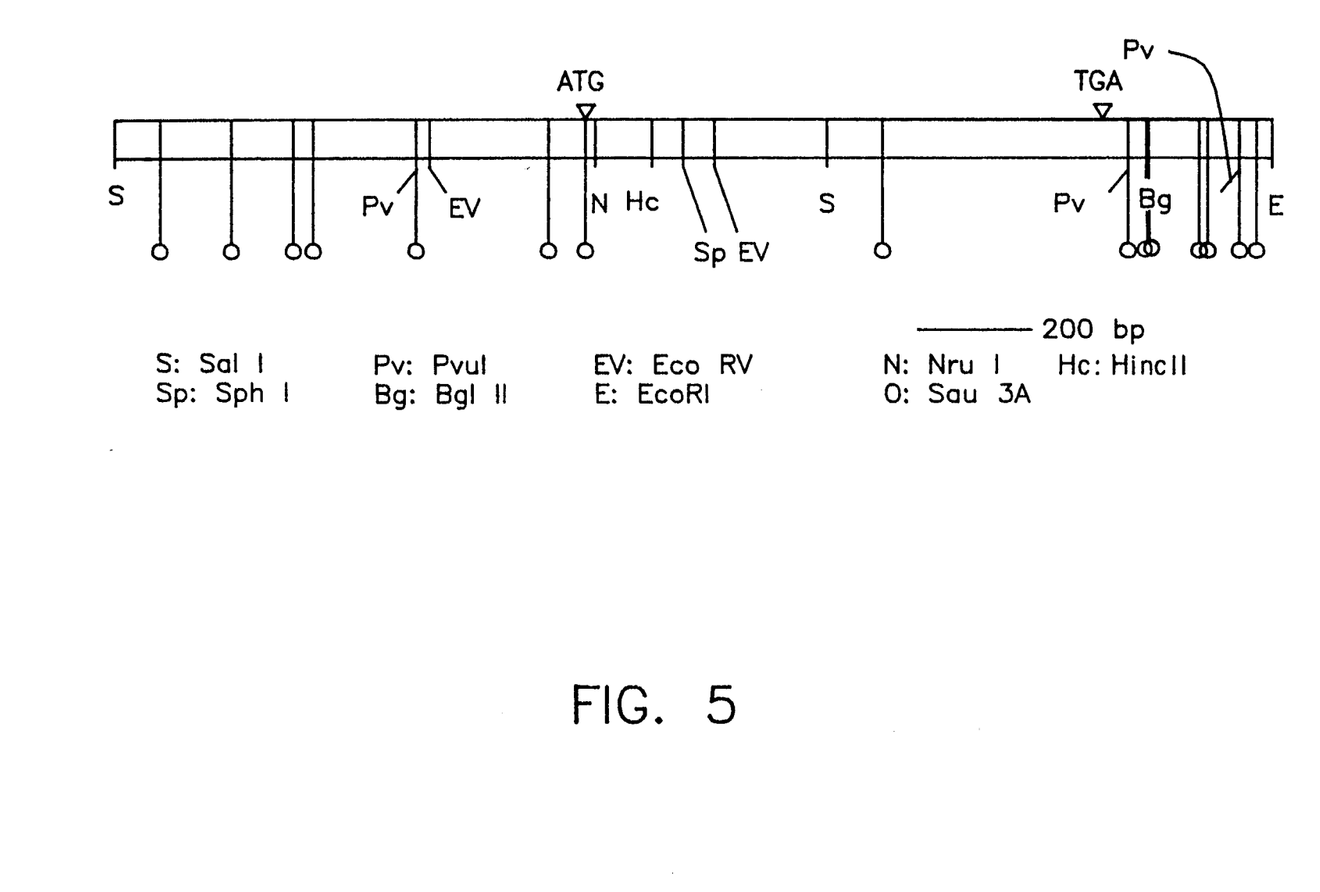
FIG. 5 illustrates the restriction map of the SSE fragment of plasmid p7A6Δ4.

The recombinant plasmid p7A6 was prepared by the alkaline method of Birnboim and Doly (Nucleic Acids Research 7, 1513–1523 [1979]) and fragmented with the following restriction enzymes:

EcoRI, EcoRV, HaeIII, HincII, NruI, Sal I, Sau 3A, XhoII, BamHI, BglII, Dra I, Hind III and Sma I. EcoRI, HincII, NruI and Sal I digested the insert DNA of p7A6 (25kb) into 8 to 11 fragments. HaeIII, Sau 3A and XhoII generated numerous numbers of fragments. Sal I was selected for the first step of subcloning.

p7A6 was partially digested with Sal I, ligated with dephosphorylated pVK102 DNA digested with Sal I. The DNA mixture was transferred to *E. coli* S17-1 by transformation and then to *G. oxydans* OX-4 by bi-parental conjugation. The smallest subclone, p7A6Δ2, was isolated from the mini-resting screening of 200 transconjugants and its size of the insert was 9.2kb (FIG. 4-(a)). Second subcloning was conducted by a deletion of the fragment $E_1$-$E_2$ of p7A6Δ2. p7A6Δ3 (FIG. 4-(b)) thus obtained was further shortened by deletion of the fragment $E_{178}$ -$Sm_3$. The resulting subclone, p7A6Δ4 (FIG. 4-(c)), contained a 3.1kb insert in pVK102 with a small deletion of $Sm_2Sm_3$ in the vector DNA. The detailed restriction map of the 3.1 kb $S_1$-$S_2$-$E_{\frac{1}{2}}$ (SSE) fragment is illustrated in FIG. 5.

Many modifications and variations of this invention may be made without departing from its spirit and scope, as will become apparent to those skilled in the art. The specific embodiments described herein are offered by way of example only, and the invention is to be limited only by the terms of the appended claims and their equivalents.

We claim:

1. A shuttle vector comprising a replication origin functional in *Escherichia coli*, a replication origin functional in *Gluconobacter oxydans* selected from the group consisting of a replication origin of *Gluconobacter oxydans*, a replication origin of an endogenous plasmid of *Gluconobacter oxydans* and a replication origin of an endogenous phage of *Gluconobacter oxydans* and a Mob site, wherein the vector is PGE1.

2. A shuttle vector as recited in claim 1 containing at least one marker gene.

3. A vector as recited in claim 2, wherein at least one of said marker gene is an antibiotic resistance gene.

4. A vector as recited in claim 1, containing at least one insert wherein said insert is selected from the group consisting of DNA sequences having multicloning sites, expression control sequences, cos sites, terminator sequences, ribosome binding sites, DNA sequences encoding signal peptides, proteins or proteins containing signal peptides.

5. A transformed strain of *Escherichia coli* wherein said strain contains a shuttle vector, which vector comprises a replication origin functional in *Escherichia coli*, a replication origin functional in *Gluconobacter oxydans* selected from the group consisting of a replication origin of *Gluconobacter oxydans*, a replication origin of an endogenous plasmid of *Gluconobacter oxydans*, a replication origin of an endogenous phage of *Gluconobacter oxydans* and a Mob site, wherein the vector is PGE 1.

6. A transconjugate of a microorganism of the genus Gluconobacter or Acetobacter wherein said transconjugate contains a shuttle vector, the vector comprising a replication origin functional in *Escherichia coli*, a replication origin functional in *Gluconobacter oxydans* selected from the group consisting of a replication origin of *Gluconobacter oxydans*, a replication origin of an endogenous plasmid of *Gluconobacter oxydans* and a replication origin of an endogenous phage of *Gluconobacter oxydans* and a Mob site, wherein the vector is PGE 1.

7. A process for producing a transconjugate of a microorganism of the genus Gluconobacter or Acetobacter comprising conjugally mating the microorganism with a transformed or transfected *Escherichia coli* containing a shuttle vector wherein the vector comprises a replication origin functional in *Escherichia coli*, a replication origin functional in *Gluconobacter oxydans* selected from the group consisting of a replication origin of *Gluconobacter oxydans*, a replication origin of an endogenous plasmid of *Gluconobacter oxydans* and a replication origin of an endogenous phage of *Gluconobacter oxydans* and a Mob site, wherein the vector is PGE 1.

8. A process for producing a polypeptide comprising forming a shuttle vector, wherein the vector comprises a replication origin functional in *Escherichia coli*, a replication origin functional in *Gluconobacter oxydans* selected from the group consisting of a replication origin of *Gluconobacter oxydans*, a replication origin of an endogenous plasmid of *Gluconobacter oxydans* and a replication origin of an endogenous phage of *Gluconobacter oxydans*, a Mob site and a DNA sequence coding for the polypeptide operatively linked with an expression control sequence wherein the vector is PGE 1, transforming an *Escherichia coli* with the vector, transconjugating a microorganism of the genus Gluconobacter or Acetobacter with said *Escherichia coli*, and culturing the transconjugate to allow expression of the polypeptide, and recovering said polypeptide and recovering said polypeptide.

* * * * *

UNITED STATES PATENT AND TRADEMARK OFFICE
CERTIFICATE OF CORRECTION

PATENT NO. : 5,399,496
DATED : March 21, 1995
INVENTOR(S) : Akio Fujiwara, et al It is certified that error appears in the above-indentified patent and that said Letters Patent is hereby corrected as shown below:

Column 16, lines 20-21 ", and recovering said polypeptide and recovering said polypeptide" should read -- and recovering said polypeptide. --

Signed and Sealed this

Nineteenth Day of September, 1995

*Attest:*

BRUCE LEHMAN

*Attesting Officer*     *Commissioner of Patents and Trademarks*